United States Patent [19]

Parisi

[11] Patent Number: 4,808,153
[45] Date of Patent: Feb. 28, 1989

[54] DEVICE FOR REMOVING PLAQUE FROM ARTERIES

[75] Inventor: Tulio T. Parisi, San Diego, Calif.

[73] Assignee: Ultramed Corporation, San Diego, Calif.

[21] Appl. No.: 931,514

[22] Filed: Nov. 17, 1986

[51] Int. Cl.$^4$ .............................................. A61B 17/20
[52] U.S. Cl. ..................................... 604/22; 128/305; 433/91
[58] Field of Search ............. 604/22; 128/303 R, 305, 128/66; 433/91

[56] References Cited

U.S. PATENT DOCUMENTS

| | | | |
|---|---|---|---|
| 3,352,303 | 11/1967 | Delaney | 128/303 R |
| 3,433,226 | 3/1969 | Boyd | 128/305 |
| 3,565,062 | 2/1971 | Kurls | 128/303 R |
| 4,531,934 | 7/1985 | Kossovsky et al. | 604/22 |
| 4,561,438 | 12/1985 | Bonnet et al. | 604/22 |
| 4,634,420 | 1/1987 | Spinosa et al. | 604/22 |

*Primary Examiner*—C. Fred Rosenbaum
*Assistant Examiner*—J. L. Kruter
*Attorney, Agent, or Firm*—Ellsworth R. Roston; Charles H. Schwartz

[57] ABSTRACT

A hollow member is made from a material such as titanium with properties of vibrating longitudinally. The interior surface of the hollow member is preferably quite smooth. At least one member is disposed on the hollow member and is provided with properties of vibrating longitudinally at an ultrasonic frequency when energized. Preferably a plurality of such vibratory members are disposed around the periphery of the hollow members. The vibratory members may be crystals. The vibratory members are preferably disposed in a socket in the hollow member so that the vibratory members are flush with the hollow member. A hollow catheter made from a pliant material such as a silicone rubber is disposed on the hollow member and the vibratory members and is preferably provided with a substantially smooth inner periphery and a substantially smooth outer periphery along its length. The forward end of the catheter preferably covers the forward end of the hollow member and preferably has a blunt disposition. The hollow member, the vibratory members and the catheter are disposed in an artery and are movable along the artery to emulsify plaque on the interior wall of the artery without damaging the interior wall of the artery. The emulsified plaque is removed as by a vacuum through the hollow member and the catheter.

9 Claims, 1 Drawing Sheet

DEVICE FOR REMOVING PLAQUE FROM ARTERIES

This invention relates to apparatus for removing plaque from the interior wall of an artery. More particularly, the invention relates to apparatus movable along the inner wall of an artery and constructed to emulsify plaque deposited on the inner wall and to remove the emulsified plaque.

Problems relating to the human heart are probably more serious than any other problems, particularly in human beings of middle and advanced age. The heart problems often occur instantaneously and unexpectedly in human beings so that such human beings do not have an opportunity to take measures to minimize the effects of such heart problems.

A considerable effort has been made to alleviate problems relating to heart attacks. These attempts have included precautionary measures in advance of a heart attack. Examples of this are bypass operations. These attempts have also involved measures after a heart attack to alleviate any permanent damage to the heart.

Damage to the heart also often results from the accumulation of plaque on the interior wall of an artery. This plaque tends to restrict the flow of fluid through the artery. As a result, the heart has to work harder to pump blood through the human body than it would have had to work if the plaque did not accumulate. This has produced enlargements in the heart. Furthermore, if the restriction resulting from the accumulation of plaque on the interior wall of the artery becomes sufficiently advanced, the human being may suffer a heart seizure which may permanently injure the human being. In a sufficiently disturbing number of cases, the human being may even die.

As a result of the considerable effort made to alleviate problems relating to heart attacks, considerable advances have been made in treating human beings both before and after heart attacks occur in such human beings. However, in spite of such advances, considerable problems still remain, as may be seen from the fact that problems relating to heart attacks are still probably more serious than any other form of human malady. For example, plaque still accumulates on the inner wall of an artery and restricts the ability of the heart to pump blood through the artery.

This invention provides apparatus for removing plaque from an inner wall of an artery. The apparatus is able to move along the inner wall of the artery without damaging the artery and is able to emulsify the plaque on the inner wall of the artery as it moves along the artery. The apparatus is then able to remove the emulsified plaque so that the inner wall of the artery is completely open to the flow of blood through the artery. In this way, the apparatus of this invention is able to inhibit any heart attacks in a human being because of an accumulation of plaque on the inner wall of an artery.

In one embodiment of the invention, a hollow member is made from a material such as titanium and is provided with properties of vibrating longitudinally. The interior surface of the hollow member is preferably quite smooth. At least one member is disposed on the hollow member and is provided with properties of vibrating longitudinally at an ultrasonic frequency when energized. Preferably a plurality of such vibratory members are disposed around the periphery of the hollow members. The vibratory members may be crystal.

The vibratory members are preferably disposed in a socket in the hollow member so that the vibratory members are flush with the hollow member.

A catheter made from a pliant material such as a silicon rubber is disposed on the hollow member and the vibratory members and is preferably provided with a substantially smooth inner periphery and a substantially outer periphery along its length. The forward end of the catheter preferably covers the forward end of the hollow member and preferably has a blunt disposition.

The hollow member, the vibratory members and the catheter are disposed in an artery and are movable long the artery to emulsify plaque on the interior wall of the artery without damaging the interior wall of the artery. The emulsified plaque is removed as by vacuum through the hollow member and the catheter.

Figure 1:
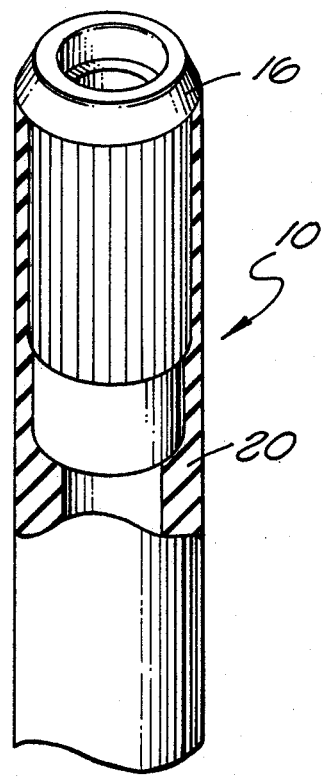
FIG. 1 is perspective view of apparatus constituting one embodiment of this invention for removing plaque from an inner wall of an artery.

In one embodiment of the invention apparatus generally indicated at 10 is provided or removing plaque from an inner wall of an artery 11. The apparatus 10 includes a hollow member 12 made from a suitable material such as titanium. Titanium is advantageous because it is strong and light and because it is able to vibrate longitudinally. The hollow member 12 includes a socket 13 and further includes at its forward end a lip portion 14 partially defining the socket 12. A tubular portion 16 extends forwardly and inwardly in the hollow member 12 from the lip portion 14 to provide the hollow member 12 with a blunt forward end. As will be seen in FIGS. 1 and 2, the blunt forward and 17 is preferably chamfered.

Figure 2:
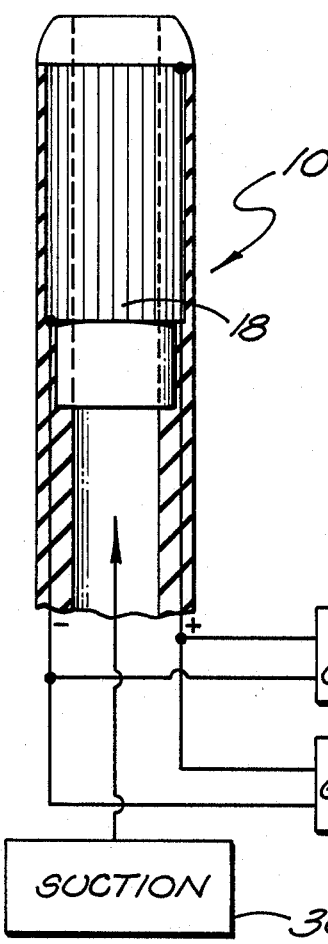
FIG. 2 is a schematic elevational view, partially in section, of the apparatus shown in FIG. 1 and includes, in schematic block form, additional electrical and pneumatic stages for operating such apparatus.

At least one vibratory member such as a crystal 18 is disposed on the hollow member 12 within the socket 13. Preferably a plurality of crystals 18 are disposed in the socket as shown in FIGS. 1 and 2. Each of the crystals 18 has a segmented configuration and extends longitudinally in the socket 13. Preferably as many as sixteen (16) of such crystal elements may be disposed annularly around the periphery of the socket 13 so as to be disposed in juxtaposed relationship to one another. The crystals 18 may be constructed in a conventional manner to vibrate in the longitudinal direction at an ultrasonic frequency when energized.

A catheter 20 having pliant characteristics envelops the crystals 18. The catheter 20 is hollow and is preferably made from a suitable material such as a silicon rubber. Preferably the catheter 20 is disposed at its forward end against the extension 16 in the hollow member 12.

The crystals 18 may be energized at the ultrasonic frequency as by a generator indicated in block form at 22. The times for energizing the crystals may be controlled by a microcomputer indicated in block form at 24. The generator 22 and the microcomputer 24 may be constructed in a manner well known in the art.

Figure 3:
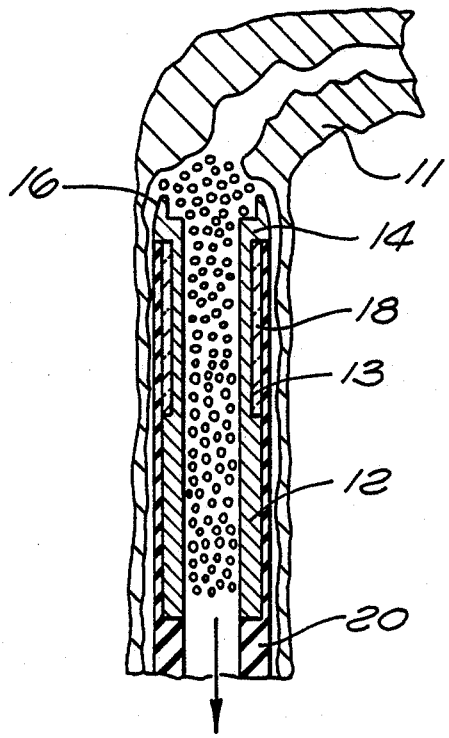
FIG. 3 is an enlarged sectional view somewhat similar to that shown in FIG. 2 and schematically illustrates the operation of the apparatus constituting this invention.

When the crystals are energized by the signals from the generator 22, they vibrate longitudinally and produce corresponding vibrations in the hollow member 12. These vibrations are transferred to the catheter 20 to produce vibrations in the tubular portion 16 of the catheter. As the hollow member 12 vibrates at its forward end, it engages the plaque on the inner wall of the artery 11 in FIG. 3. This movement tends to remove the plaque from the inner wall of the artery 11.

The removal of the plaque from the inner wall of the artery 11 is facilitated by the heat generated as a result of the movement of the hollow member 12 and the catheter 20. This heat tends to emulsify the plaque on the inner wall of the artery. This emulsification facilitates the movement of the plaque into the hollow interior of the hollow member 12 and the catheter 20. The movement of the plaque through the hollow member 12 and the catheter 20 is facilitated by a vacuum applied to such hollow interiors by apparatus indicated in block form at 30 in FIG. 2.

The apparatus described above has certain important advantages. It can be easily moved along the inner wall of the artery 11 because of the pliant characteristics of the catheter 20. This movement is facilitated because the catheter 20 has a uniform diameter at every position along its length. Furthermore, the forward end of the hollow member 12 has a smaller diameter than the diameter at other positions along the length of the hollow member and the catheter 20. This insures that the apparatus of this invention will not scratch or otherwise damage the artery 11 as the apparatus moves along the artery.

The apparatus of this invention also has other important advantages. For example, since the inner wall of the hollow member 12 has a smooth and uniform surface, the plaque being sucked through the hollow member as by vacuum cannot stick to the inner wall of the hollow member or otherwise accumulate on the inner wall of the hollow member.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

I claim:

1. In combination for removing an obstruction from the interior wall of an artery,
   a member made from a light and strong material and provided at its forward end with a hollow interior defined by an interior wall having a smooth configuration and with characteristics of vibrating at an ultrasonic frequency,
   means disposed on the member at a position abutting the forward end of the member and providing energy at the ultrasonic frequency for vibrating the member at the ultrasonic frequency to emulsify the obstruction,
   a hollow tube covering the member and the ultrasonic energy means and made from a pliant material and extending rearwardly past the rear ends of the member and the ultrasonic energy means to facilitate the movement of the tube, the member and the energy means along the interior wall of the artery, and
   the hollow tube covering the member and the ultrasonic energy means along the length of the ultrasonic energy means and the member having a chamfered configuration at its forward end to facilitate the removal of the obstruction from the interior wall of the artery by emulsification of the plaque in accordance with the vibrations of the member at the ultrasonic frequency,
   the member being provided with a socket at its outer periphery to receive the ultrasonic energy means and to provide the hollow tube with substantially uniform external dimensions along the length of the tube when the ultrasonic means is disposed in the socket.

2. In combination for removing plaque from the interior wall of an artery,
   a hollow member made from a material having characteristics of vibrating at an ultrasonic frequency,
   means disposed on the hollow member at the forward end of the hollow member for positioning the forward end of the member in abutting relationship with obstruction and having characteristics of vibrating at an ultrasonic frequency, when energized, to produce a vibration of the hollow member at the ultrasonic frequency, and
   a hollow tube made from a pliant material and enveloping the hollow member and the ultrasonic vibrating member
   the member having a chamfered forward end to facilitate the removal of the plaque from the interior wall of the artery, in accordance with the longitudinal vibrations of the member at the ultrasonic frequency, without damaging such interior wall, and
   means for providing for a removal through the hollow member and the hollow tube of the plaque removed by emulsification from the interior wall of the artery.

3. In a combination as set forth in claim 2,
   the ultrasonic energy means constituting at least one crystal disposed around the periphery of the hollow member.

4. In a combination as set forth in claim 2,
   the ultrasonic energy means constituting a plurality of crystals disposed around the periphery of the hollow member,
   the hollow member being provided with a shoulder at its forward end to receive the crystals in the plurality, and
   the tube enveloping the crystals and the member having a substantially uniform internal disposition along its length.

5. In a combination as set forth in claim 4,
   the hollow member being made from titanium and the tube being made from a nylon.

6. In a combination as set forth in claim 5, the chamfered end of the member extending forwardly beyond the forward end of the tube and the tube extending rearwardly beyond the rear end of the member.

7. In a combination as set forth in claim 6,
   the chamfered end of the member being chamfered and the inner surfaces of the hollow member and the tube being smooth and substantially continuous with each other.

8. In combination for removing an obstruction from the interior wall of an artery,
   means having a hollow configuration and constructed to provide energy at an ultrasonic frequency,
   a member for dissolving the obstruction on the walls of the artery in accordance with vibrations of the member at the ultrasonic frequency, the member having a forward end for abutting the plaque on the walls of the artery, the ultrasonic energy means being disposed on the member at a position adjacent the forward end of the member for applying energy at the ultrasonic frequency to the member to vibrate the member at the ultrasonic frequency, and a tube disposed on the member and the ultrasonic energy means and made from a pliable material to facilitate the movement of the member and the ultrasonic energy means along the interior wall of an artery, the tube extending rearwardly past the rear ends of the ultrasonic energy means and the member, the member being formed to define a chamfered edge at its forward end for facilitating the removal of the obstruction from the interior wall of the artery by emulsification in accordance with the vibrations of the member at the ultrasonic frequency, the inner surfaces of the member and the tube being smooth and being substantially continuous with each other, the member being provided with a socket on its periphery, the ultrasonic energy means being formed from a plurality of crystals disposed in an annular relationship in the socket on the periphery of the member and the tube covering the crystals.

9. In combination for removing an obstruction from the interior wall of an artery, means having a hollow configuration and constructed to provide energy at an ultrasonic frequency, a member for dissolving the obstruction on the walls of the artery in accordance with vibrations of the member at the ultrasonic frequency, the member having a forward end for abutting the plaque on the walls of the artery.

the ultrasonic energy means being disposed on the member at a position adjacent the forward end of the member for applying energy at the ultrasonic frequency to the member to vibrate the member at the ultrasonic frequency, and a tube disposed on the member and the ultrasonic energy means and made from a pliable material to facilitate the movement of the member and the ultrasonc energy means along the interior wall of an artery, the tube extending rearwardly past the rear ends of the ultrasonic energy means and the member, the member being formed to define a chamfered edge at its forward end for facilitating the removal of the obstruction from the interior wall of the artery by emulsification in accordance with the vibrations of the member at the ultrasonic frequency, the member being provided with a shoulder at its external periphery to receive the ultrasonic energy means at the position abutting the forward end of the member, the member being provided with a socket, the ultrasonic means being formed from a plurality of crystals disposed in the socket in the member in annularly spaced relationship to one another and the tube covering the member and the ultrasonic means along the length of the ultrasonic means.

* * * * *